(12) United States Patent
Jeppsson et al.

(10) Patent No.: US 7,559,913 B1
(45) Date of Patent: Jul. 14, 2009

(54) METHOD AND DEVICE FOR PD CYCLERS

(75) Inventors: Jan-Bertil Jeppsson, Lomma (SE); Mikael Axelsson, Furulund (SE); Staffan Bengtsson, Göteborg (SE); Pär Löfgren, Lund (SE); Robert Hlustik, Lund (SE); Silivia Recupero, Medolla (IT)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 10/204,186

(22) PCT Filed: Feb. 28, 2000

(86) PCT No.: PCT/SE00/00379

§ 371 (c)(1), (2), (4) Date: Jan. 7, 2003

(87) PCT Pub. No.: WO01/64263

PCT Pub. Date: Sep. 7, 2001

(51) Int. Cl.
*A61M 1/00* (2006.01)

(52) U.S. Cl. .................................................. 604/29

(58) Field of Classification Search .............. 604/29, 604/27, 28, 30, 33
See application file for complete search history.

(56) References Cited

U.S. PATENT DOCUMENTS

| | | | |
|---|---|---|---|
| 3,709,222 A | 1/1973 | DeVries | |
| 4,096,859 A * | 6/1978 | Agarwal et al. | 604/28 |
| 4,396,382 A | 8/1983 | Goldhaber | |
| 4,560,472 A | 12/1985 | Granzow et al. | |
| 4,620,846 A | 11/1986 | Goldberg et al. | |
| 4,950,230 A * | 8/1990 | Kendell | 604/28 |
| 5,141,492 A * | 8/1992 | Dadson et al. | 604/28 |
| 5,843,049 A | 12/1998 | Heilmann et al. | |
| 5,925,011 A * | 7/1999 | Faict et al. | 604/29 |
| 6,508,880 B2 * | 1/2003 | Vodakov et al. | 117/202 |
| 6,580,800 B1 * | 6/2003 | Yamasaki et al. | 381/379 |
| 6,585,682 B1 * | 7/2003 | Haraldsson et al. | 604/29 |

FOREIGN PATENT DOCUMENTS

| | | | |
|---|---|---|---|
| EP | 0777111 | * | 4/1997 |
| EP | 777111 | | 6/1997 |
| EP | 0777111 | * | 6/1997 |
| EP | 0 799 610 | | 10/1997 |
| WO | 94 20154 | | 9/1994 |
| WO | 95 20985 | | 8/1995 |
| WO | WO 95/20985 | * | 8/1995 |
| WO | WO 95/20985 | * | 10/1995 |
| WO | 97 07837 | | 3/1997 |

OTHER PUBLICATIONS

International Search Report issued in European application EP 07 00 9572, Jul. 27, 2007, 4 pages.

* cited by examiner

*Primary Examiner*—Nicholas D Lucchesi
*Assistant Examiner*—Christopher D Koharski
(74) *Attorney, Agent, or Firm*—Pillsbury Winthrop Shaw Pittman LLP

(57) ABSTRACT

PD-cycler and tube set therefor and a method for use thereof. The tube set includes a transfer member for automatic transfer of possibly remaining contents in supply bags or heater bags of the tube set to a waste receiver. A separate connection unit is arranged in connection with a valve pack of the PD-cycler. The connection unit has a rod of ferromagnetic material which allows an indication that the tube set is in the correct position. The beater and drain bags are combined into a double bag which is supported by a yoke in a folded state, which is unfolded upon application into the PD-cycler.

19 Claims, 9 Drawing Sheets

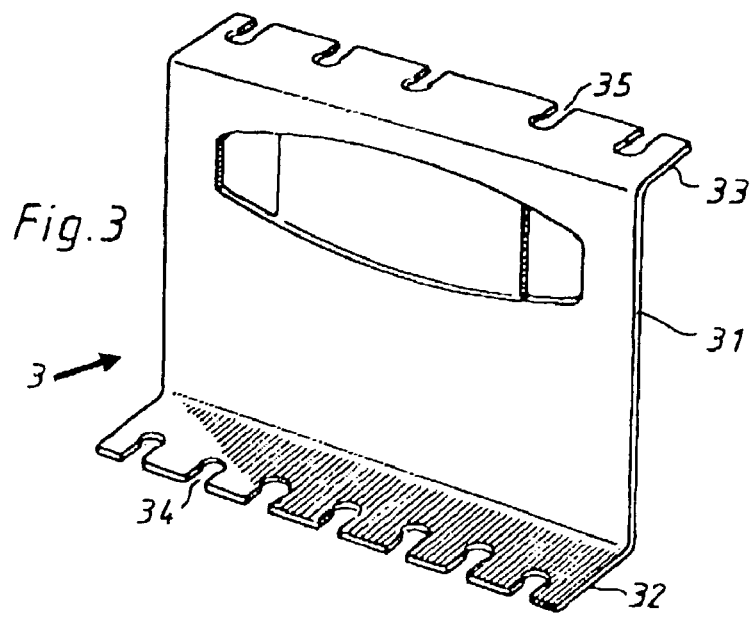
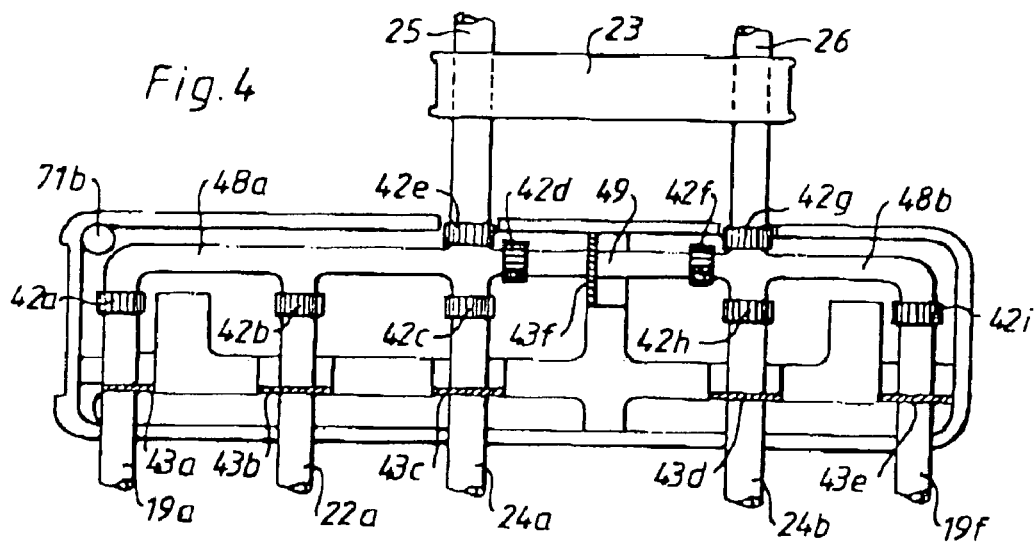
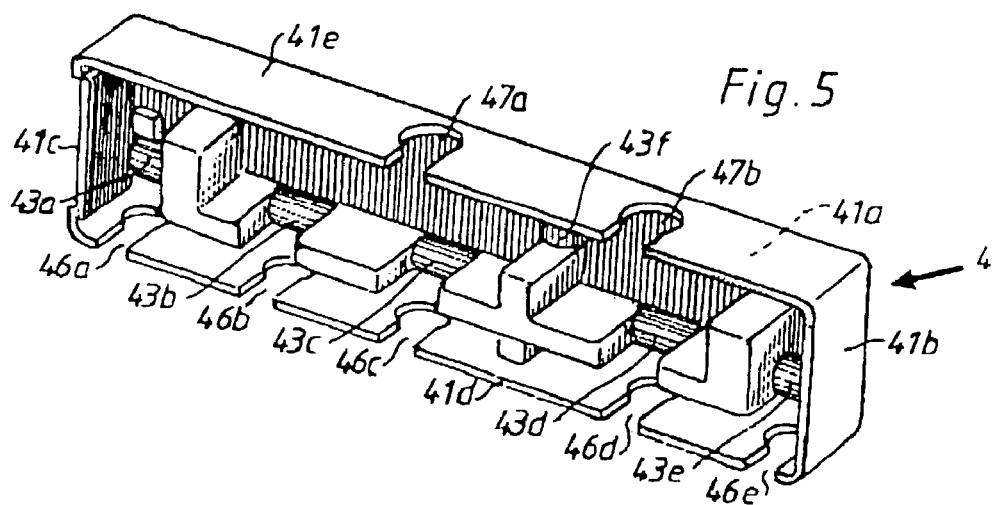

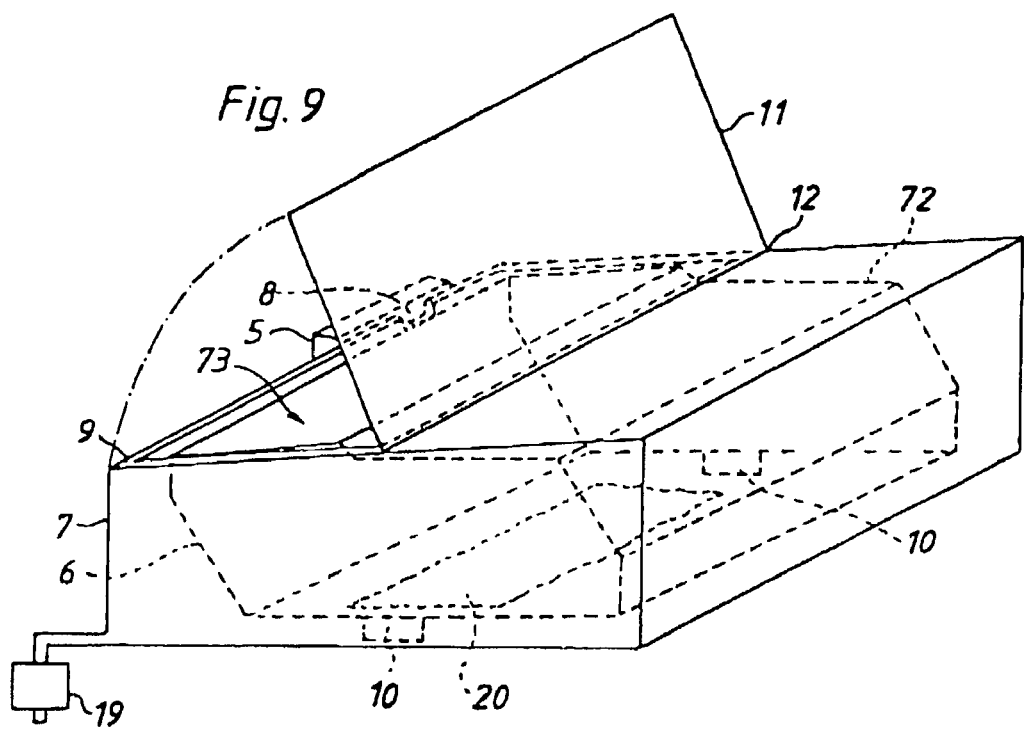
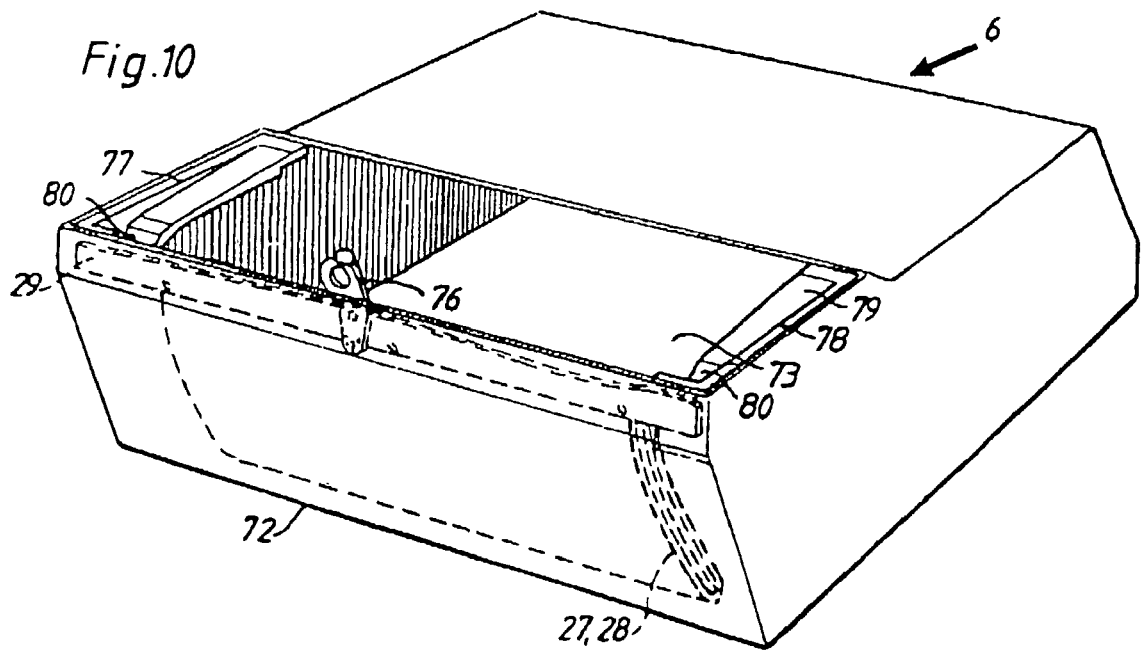

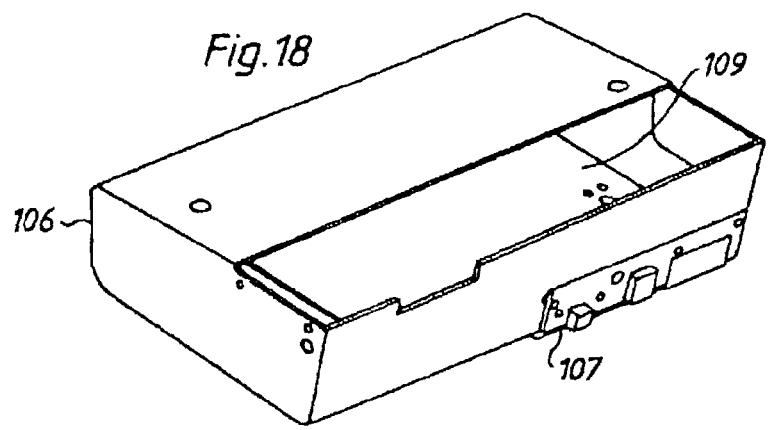
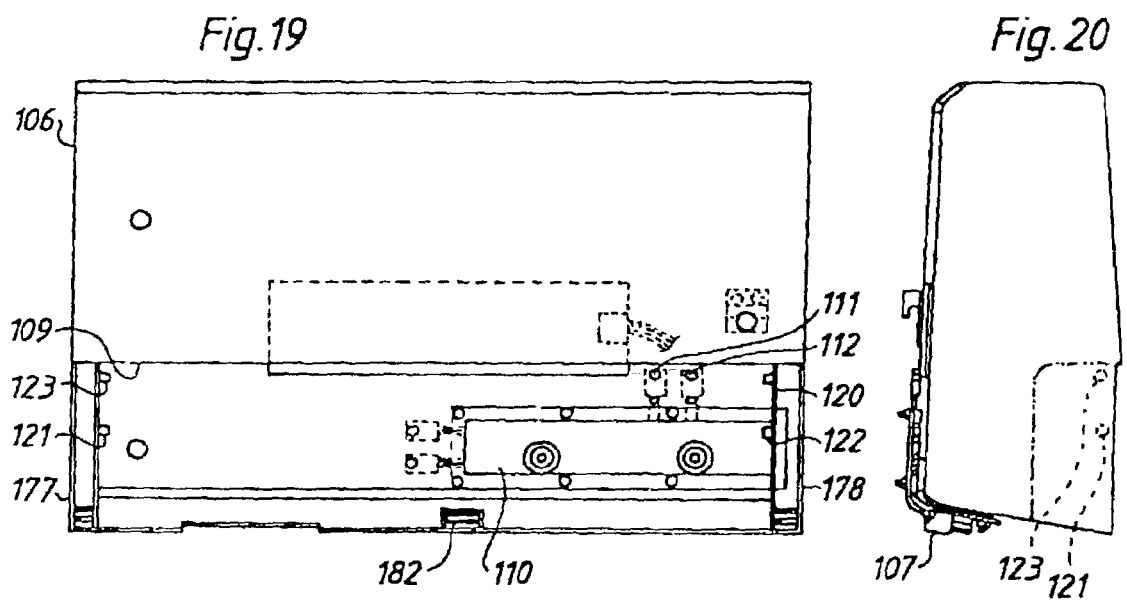
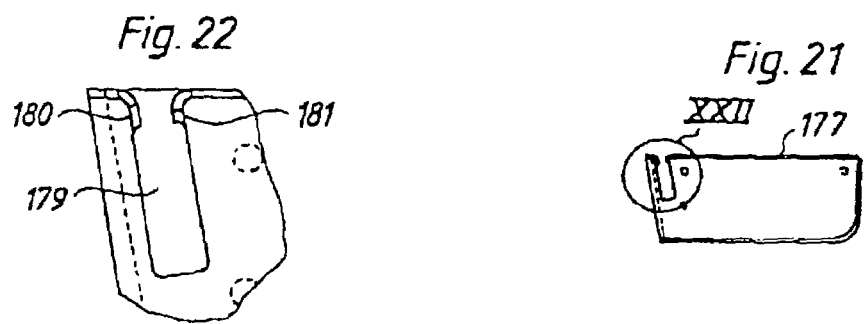

METHOD AND DEVICE FOR PD CYCLERS

FIELD OF THE INVENTION

The invention relates to a PD-cycler which is used in connection with peritoneal dialysis, PD, for fill and drain of a peritoneal dialysis fluid or PD-fluid, especially during Automated Peritoneal Dialysis, APD.

BACKGROUND ART

A PD-cycler is described in our international patent application published under number WO 95/20985. This PD-cycler is arranged between a source of PD-fluid and a PD patient. The patient has a catheter implanted, which extends from the abdominal cavity inside the patient's peritoneal membrane and through the skin to a catheter coupling located outside the body. The PD-cycler may fill and drain PD-fluid by means of the catheter to and from the patient's peritoneal cavity in order to carry out peritoneal dialysis.

With the form of treatment which is most prevailing nowadays, namely CAPD, Continuous Automated Peritoneal Dialysis, the patient connects the catheter coupling to a tube set which includes a supply bag for PD-fluid and a drain bag. Valves and/or clamps arranged on the tube set are configured so that the patient can drain the contents of the peritoneal cavity into the drain bag, by placing the drain bag on the ground and allowing the fluid to run out with the aid of gravitational force. After that, the valves and/or the tube clamps are configured so that fresh PD-fluid can be filled into the peritoneal cavity from the supply bag, which is positioned in a high position on a stand, by the aid of gravitational force. Then, the patient keeps the PD-fluid in the peritoneal cavity for about 4 hours, after which time a new fill phase takes place. During the night, no fill and drain takes place, and instead one and the same PD-fluid is kept during the whole night, or, alternatively, the peritoneal cavity is drained from PD-fluid.

With the aid of the aforementioned PD-cycler, the replacement can be automated so that no manual action is required apart from the initial connection and final disconnection, which means that the PD-fluid exchanges can take place during the night when the patient is sleeping.

The PD-cycler is normally used for APD which preferably takes place at night, with the patient constantly connected to the PD-cycler. With this form of treatment the patient is completely free during the day. In order to increase the effectiveness, the patient may, however, do one or more fluid exchanges during the day. The treatment form APD is normally more effective than CAPD, inter alia because a larger amount of PD-fluid may be used. The PD-cycler can also be used for any of the currently known peritoneal dialysis treatment methods.

The PD-cycler which is described in the aforementioned WO 95/20985 constitutes an effective solution to the task of carrying out peritoneal dialysis and in particular APD. One disadvantage with this arrangement is however that the tube set which is used has to be placed on the PD-cycler so that the tubes pass through electromagnetically controlled valves which control the operation. There is a risk that the patient will place the tubes so that they pass through the wrong clamps by turning the tube set incorrectly, with the consequent risk of an incorrect treatment.

Normally this problem is solved by using some type of "organizer" which systematises the tubes and may include valve functions. Such a device is disclosed in WO 94/20154, where this organizer consists of a separate plastic unit, to which unit a number of tubes are connected. The unit is placed in a separate holder in the PD-cycler and electromagnetically controlled actuation devices act on valves and membranes included in the unit for producing valve functions and pump functions. The disadvantage of these organizers is that they are often very complicated and thus expensive to manufacture.

SUMMARY OF THE INVENTION

A first object of the invention is to provide a valve pack arranged on the PD-cycler and a separate tube set, which allow extra functions which have previously not been present on such a PD-cycler.

A second object of the present invention is to provide a tube set comprising a connection unit, in particular intended for a PD-cycler of the type disclosed in WO 95/20985, which connection unit is simple and therefore cheap to manufacture, as well as including safety devices so that patient safety is prioritised.

A third object of the invention is to provide a tube set which is simple to apply to the PD-cycler.

A fourth object of the invention is to provide a valve pack having a soft valve operation, which is mild for the patient.

A fifth object is to provide a PD-cycler having improved safety.

A method and a device is thereby provided for operating a tube set intended for peritoneal dialysis by means of a PD-cycler, whereby the tube set comprises a heater bag for temporarily storing and heating of a fresh PD-fluid obtained from a source of PD-fluid, such as at least one supply bag, and one drain bag for draining of spent PD-fluid from a patient and for further transport to a waste receiver, possibly in the form of an collection bag, whereby the PD-cycler comprises a valve pack intended for acting on the tubes in said tube set to control the flows. In accordance with the invention, any PD-fluid, which might still be in the supply bag after completion of a PD-treatment, is transported to the heater bag and/or the drain bag by activating valves in the valve pack, after which all the fluid in the heater bag and/or the drain bag is transferred to the waste receiver by activation of a separate valve which opens a connection from the heater bag and/or the drain bag to the drain. This function constitutes an extra function which has not until now been present on such a PD-cycler.

The PD-cycler is suitably provided with a scales container, in which said heater bag and drain bag are positioned, whereby said flows are achieved by arranging an over-pressure or under-pressure inside said scales container.

The transfer of the contents of the heater bag preferably occurs through a separate transfer member which connects the heater bag with the drain bag, whereby the valve pack acts on said transfer member in order normally to close the transfer member but to keep it open during the aforementioned transfer.

In one embodiment of the invention the valve pack comprises valve rods which co-operate with abutments, for example arranged in a connection unit of the tube set, and where the valve rods are arranged to clamp a tube between themselves and the abutment for closing off the flow therein, whereby the valve rods are arranged to be able to partially stop the flow in the tube in order to achieve a soft valve function which is mild for the patient.

In accordance with the invention there is a connection unit arranged in the tube set, whereby said transfer member is arranged in the connection unit. In the connection unit there are abutments which co-operate with valve shafts in a valve pack for controlling flows in the tubes in said tube set including said transfer member.

To indicate that the connection unit is in the right position in the PD-cycler, there is a ferromagnetic rod in the connection unit, arranged to conduct magnetic radiation from a source of magnetism to a detector of magnetism. By means of this safety device, it is ensured that the PD-cycler obtains an indication that the tube set is in the correct position, which gives increased patient safety.

For simplified handling, the heater and drain bags are formed as a double bag with three plastic layers welded together at the edges. The bag is held up by a yoke along one of the sides of the bag, such that the double bag is folded along fold lines and is held by a holder member on the yoke in the folded position prior to use.

In order to allow a simplified tube set and a small and light PD-cycler, the double bag is formed with a size intended for the volumes which commonly occur in connection with PD, such as a total volume of 5-6 liters. For those patients who can use larger volumes, the PD-cycler is programmed to be able to carry out sequential draining of the patient. In a first step, spent PD-fluid is fed out to the drain bag, the volume of which is less than the original volume of used PD-fluid in the patient, until this is substantially filled, after which the contents in the drain bag is emptied in a second step to a waste receiver. The first and second steps are repeated until the patient is emptied of used PD-fluid.

Further objects, features and advantages of the invention are disclosed in more detail by the detailed description of the invention below with reference to a preferred embodiment of the invention. The invention is however not limited to the details described below but can be modified within the scope of the appended claims.

BRIEF DESCRIPTION OF THE DRAWINGS

FIG. 3 is a perspective view of the organizer in the tube set according to FIG. 2.

FIG. 4 is a view from below of the connection unit in the tube set according to FIG. 2.

FIG. 5 is a perspective view of the connection unit without tubes.

FIG. 9 is a perspective view of a scales container arranged inside the PD-cycler according to FIG. 1, whereby parts of the PD-cycler are shown schematically.

FIG. 10 is a perspective view of the scales container according to FIG. 9 with the heater bag and the drain bag in place.

FIG. 18 is a perspective view of an alternative pressure container for the PD-cyler of the invention.

FIG. 19 is a plan view of the container of FIG. 18.

FIG. 20 is a side view of the container of FIG. 18.

FIG. 21 is a side view of a guide inside the container of FIG. 18.

FIG. 22 is an enlarged side view according to the circle XXII of FIG. 21.

DESCRIPTION OF EMBODIMENTS OF THE INVENTION

Figure 1:
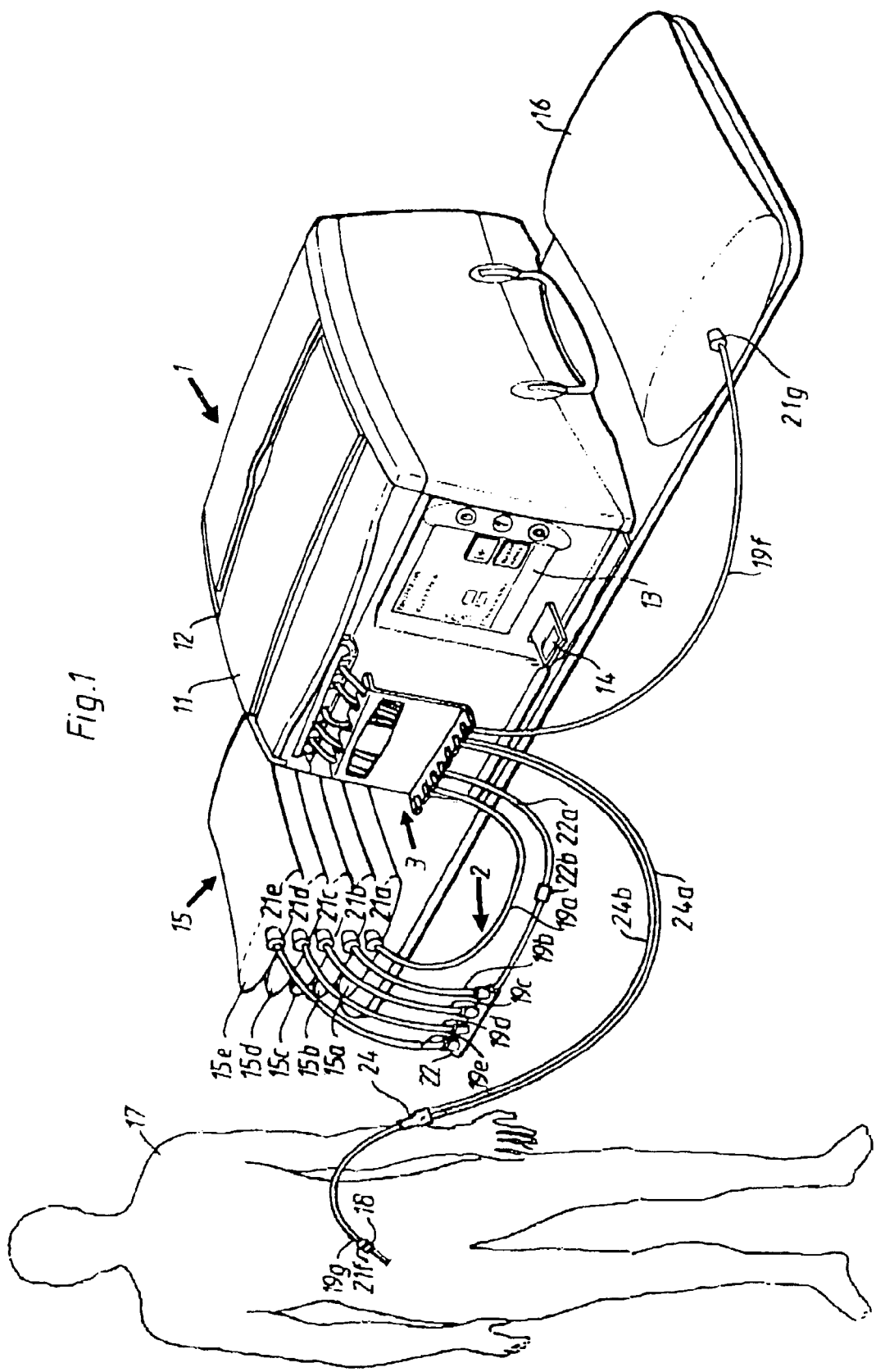
FIG. 1 is a perspective view of a PD-cycler provided with a tube set according to the invention.

FIG. 1 shows the outer casing of a PD-cycler 1 where the present invention can be used. The construction and the function of this PD-cycler is described in more detail in the aforementioned WO 95/20985 and the reader is directed to that document for further details. WO 95/20985 is incorporated herewith into the present description by reference thereto.

The PD-cycler 1 includes a cover 11 which can be folded up via hinges 12 and exposes the inside of the PD-cycler for placement of a tube set which is described in more detail below.

The PD-cycler also has a touch screen 13, where data and parameters are shown for the treatment and where the functions of the PD-cycler can be controlled. Below the touch screen 13, there is a data card 14, a so-called smart-card, where the doctor can have programmed in data for the treatment and where patient parameters can be stored. The PD-cycler can also be connected via a modem to a central computer or other equipment.

Figure 2:
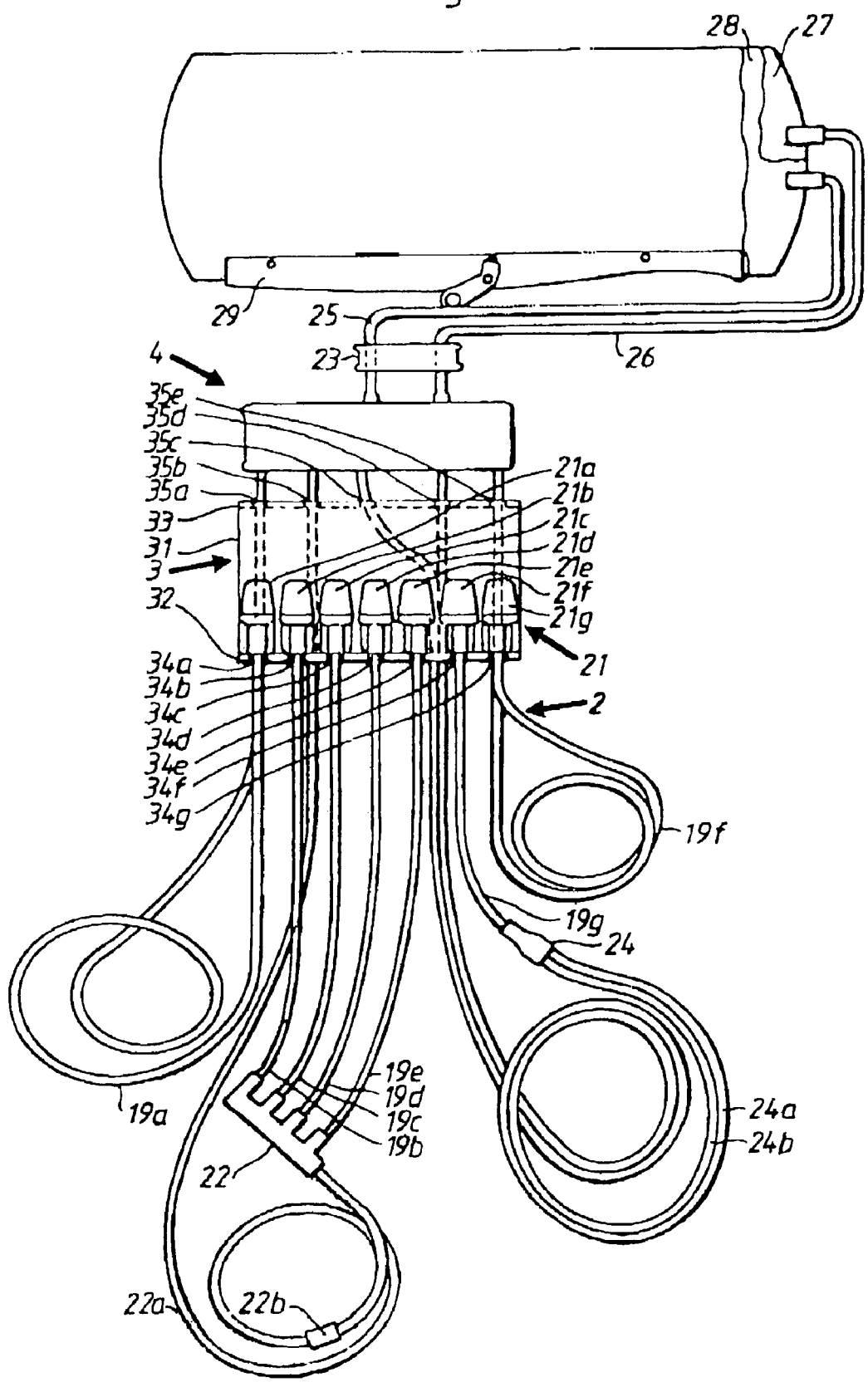
FIG. 2 is a plan view of a tube set according to the invention.

The PD-cycler is equipped with a tube set 2 which is shown in more detail in FIG. 2. The tube set is gathered by an organizer 3, which is shown in perspective in FIG. 3.

The organizer 3 consists of a plate 31 with two flanges 32 and 33 which face in opposite directions and are arranged at opposing edges of the plate 31. The lower flange 32 comprises seven notches 34 intended to fixedly hold couplings of the tube set. The upper flange 33 comprises five notches 35 intended to guide the tubes which pass out from a connection unit shown in FIGS. 4 and 5 and which is described in more detail below.

As shown in FIG. 2 a number of tubes including couplings 21 are arranged in the lower notches 34. To the left in FIG. 2 is shown a first coupling 21a arranged in a notch 34a and intended to be connected via a tube 19a to a separate supply bag 15a (see FIG. 1) containing a fluid with a special composition intended to be used during the long daytime dwell. Additionally there are couplings 21b, 21c, 21d, 21e arranged in lower notches 34b, 34c, 34d, 34e and intended to be coupled via tubes 19b, 19c, 19d, 19e to supply bags 15b, 15c, 15d, 15e (see FIG. 1) containing fluid with a standard composition for PD. Furthermore there is a coupling 21f arranged in a lower notch 34f and intended to be connected to a catheter coupling 18 of a patient 17 (see FIG. 1). Finally there is a coupling 21g arranged in a lower notch 34g and intended to be connected to an collection bag 16 (see FIG. 1) or a waste receiver.

The coupling 21a is connected to a tube 19a which extends from the separate supply bag 15a and further on the rear side of the plate 31 of the organizer 3 to an upper notch 35a and further to the connection unit 4. The couplings 21b, 21c, 21d, 21e are joined to tubes 19b, 19c, 19d, 19e which extend from respective supply bags 15*b*, 15*c*, 15*d*, 15*e* to an F-coupling 22 for parallel coupling of the supply bags 15*b*, 15*c*, 15*d*, 15*e*. A tube 22*a* extends from the F-coupling 22 on the rear side of the plate 31 of the organizer 3 and to an upper notch 35*b* and further to the connection unit 4. The coupling 21*f* is joined to a tube 19*f*, which extends from the patient's catheter coupling 18 to a branch 24. The branch is joined to two tubes 24*a*, 24*b* which extend from the branch 24 on the rear side of the plate 31 of the organiser 3 to two upper notches 35*c*, 35*d*, and further to the connection unit 4. The tubes 24*a*, 24*b* are joined by means of adhesive or in another suitable way over a large part of their length and they separate only just before the notches 35*c*, 35*d*, as shown in FIG. 2.

Thus five tubes extend up to the connection unit 4, namely tubes 19*a*, 22*a*, 24*a*, 24*b*, 19*g*. The connection unit 4 is shown in more detail in FIGS. 4 and 5 and consists of a rectangular box without a bottom. Thus a first top surface 41*a* of the connection unit 4 is planar as are the two short sides 41*b* and 41*c*. The two long sides 41*d*, 41*e* are provided with two upper notches 47*a*, 47*b* and respectively five lower notches 46*a*, 46*b*, 46*c*, 46*d*, 46*e*, which allow the five aforementioned tubes 19*a*, 22*a*, 24*a*, 24*b*, 19*g* to pass through the lower long side 41*d* and into the inside of the connection unit. "Lower" and "upper" refer to the orientation shown in FIG. 2.

As is clear from FIG. 4 three of the tubes 19*a*, 22*a*, 24*a* are connected to a first connector piece 48*a* which is further connected to a tube 25 which leads to a heater bag 27 (see below). The connector piece 48*a* is connected to the tubes 19*a*, 22*a*, 24*a*, and the tube 25 via couplings 42*a*, 42*b*, 42*c*, 42*d*, 42*e*. The other two tubes 24*b*, 19*f* are connected to a second connector piece 48*b* which is further connected to a tube 26 which leads to a drain bag 28 (see below). The connector piece 48*b* is joined to the tubes 24*b*, 19*g* and the tube 26 via couplings 42*f*, 42*g*, 42*h*, 42*i*. The tubes 25 and 26 are joined to each other via a transfer piece 49.

Opposite the five tubes 19*a*, 22*a*, 24*a*, 24*b*, 19*g* there are five abutments 43*a*, 43*b*, 43*c*, 43*d*, 43*e*. Additionally there is a separate abutment 43*f* arranged opposite the transfer piece 49. The abutments co-operate with valve shafts arranged in a valve pack in the PD-cycler (see FIG. 6) in order to selectively clamp the tubes together and thereby prevent passage of fluid through the corresponding tube. A separate valve shaft acts on the transfer piece 49, as will be explained in more detail below. By means of this valve pack the PD-cycler can be controlled to perform the desired PD treatment.

It should be understood that the connector pieces 48*a*, 48*b* can be replaced by a single connector piece, whilst the tubes 19*a*, 22*a*, 24*a*, 24*b*, 19*f*, 25, 26 are connected to the single connector piece. For this, the single connector piece may be provided with weakened portions opposite the abutments so that the necessary valve function can be obtained.

The tubes 25 and 26 pass through a through-guide 23 which leads the tubes into a scales container 6 inside the PD-cycler (see FIG. 9). The through-guide 23 provides the required sealing so that the scales container can be subjected to different pressures.

The tubes 25 and 26 lead further to a heater bag 27 and a drain bag 28. The heater bag 27 and the drain bag 28 are preferably manufactured in the form of a double bag having three plastic layers welded together along the edges (see FIG. 2).

The combined heater and drain bag is hung up in a yoke 29 arranged along one long side, see FIG. 2.

Figure 6:
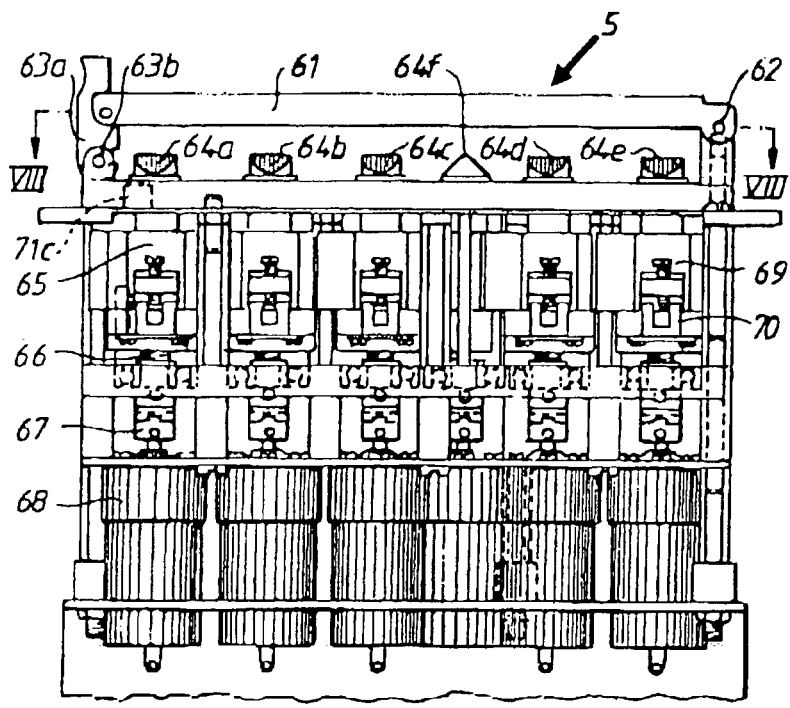
FIGS. 6, 7 and 8 are views from the long side, the short side and from above, of a valve pack arranged in the PD-cycler according to FIG. 1.
Figure 7:
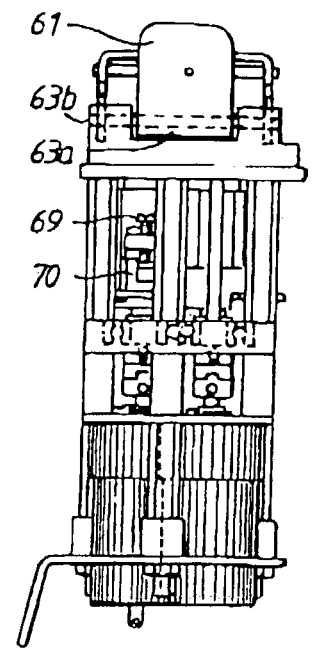
Figure 8:
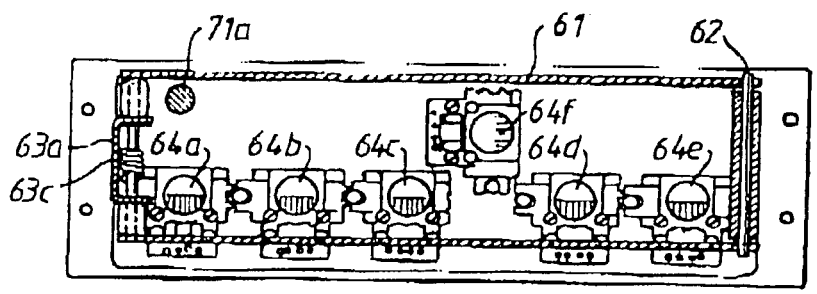

The valve pack 5 which co-operates with the tubes and the abutments in the connection unit 4 is shown in more detail in FIGS. 6, 7 and 8. The valve pack includes a cover 61 consisting of a plate with a U-formed cross-section. The cover is fixed to a shaft 62 so that it is pivotable to a position where the connection unit can be arranged under the cover. The cover is then pivoted back to its original position and a locking hook 63*a* co-operates with a locking pin 63*b* and keeps the cover in the closed position. The locking hook is biased towards the closed position by means of a spring 63*c*. The connection unit has dimensions such that it precisely fits under the cover in the U-formed recess.

Under the cover 61 there are five valve shafts 64*a*, 64*b*, 64*c*, 64*d*, 61*e*, and a separate valve shaft 64*f*. The valve shafts are arranged to co-operate with the aforementioned abutments 43*a*, 43*b*, 43*c*, 43*d*, 43*e*, 43*f*, to clamp the tubes and prevent fluid transport therethrough.

Each shaft axis 64 is fixed to a valve nut 65 which co-operates with a valve screw 66. The valve screw is supported in a ball bearing and is operated via a coupling 67 of a motor 68. The output shaft of the motor has a relatively low rotational speed due to the use of a gearbox. By activating the motor the valve shaft can be continually displaced upwardly and downwardly in order to obtain the desired valve function.

Each valve shaft is provided with an adjustment screw 69 which passes between the legs of a read-fork 70. The read-fork transmits a light beam between its legs and when the light beam is broken by the adjustment screw passing down between the legs, an electrical signal is emitted. By adjusting the adjustment screw, the upper position of the valve shaft can thereby be accurately detected, i.e. the closed position of the valve is indicated by the read-fork emitting a signal which defines that the adjustment screw is outside the legs of the read-fork. Other positions of the valve shaft can be calculated by a position sensor on the motor's output shaft which defines how many rotations or part rotations the motor has rotated. It should be understood that the adjustment screw can also be adjusted to define other positions of the valve shaft, for example a middle position, and that other positions can be calculated with the aid of the position sensor.

Since due to the motor, the valve shaft can assume any position between a completely open and completely shut tube, the valve shaft can be actuated so that a "soft" valve function is obtained. This means that when the tube is to be shut the motor is activated with a low rotational speed until it partially acts on the tube and partially clamps it against the abutment. After that, the motor can be stopped in this position a while and then be activated again for further clamping the tube. In such a way the tube is closed successively over a long time, maybe over a minute, which gives the aforementioned soft function. Of course, the valve shaft can be manoeuvred in a continual slow movement in order to perform the same soft closing function. The opening function is carried out in a similar way. By means of this soft activation of the valves, the noise from the motor will also be low which is beneficial and does not disturb the patient's sleep.

The valves are self-blocking in all positions, which means that the motors do not have to be activated if the valve shafts do not need to be displaced. This also contributes to make possible a noise reduction.

If the PD-cycler is in an alarm situation, the valves are, however, to be shut as soon as possible, whereby the motor is driven at the highest possible speed with a corresponding high noise level. This is however not a disadvantage since the patient will anyway wake up when the alarm goes.

As is clear from FIG. 8, the valve shafts are geometrically orientated to be positioned right in front of a corresponding abutment in a connection unit. It should be understood that other geometries can be used than the one shown.

During operation all of the six valve shafts apart from one are activated which means that the connection unit 4 is pressed upwards towards the cover 61, normally by five valve shafts. The locking hook 63a is thereby activated and grips securely around the corresponding locking pin 63b by the angle of the locking surface of the locking hook as is shown in FIG. 6 so that the cover cannot possibly be opened during operation. This gives extra mechanical safety against the patient removing the tube set by mistake during operation.

The cover 61 is also provided with a small permanent magnet 71a (see FIG. 8). Additionally there is a rod 71b of ferromagnetic material in the connection unit (see FIG. 4) which extends from the outside to the inside. In the valve pack there is arranged a Hall element 71c (see FIG. 6). When the connection unit is in position under the cover and the cover is closed, the Hall element 71c will be activated and will sense the presence of a magnetic field which is conducted from the permanent magnet 71a in the cover via the ferromagnetic rod 71b in the connection unit to the Hall element 71c in the valve pack. The Hall element can be replaced by a magnetic relay such as a reed element which is activated by the permanent magnet via the ferromagnetic rod 71b. The ferromagnetic rod 71b can consist of a plastic material with inbaked ferromagnetic grains or particles so that the material in the connection unit appears to be homogenous. By means of this safety device it is ensured that the PD-cycler can emit an alarm signal or, signal in another way whether the connection unit is positioned in the right position and the cover is in place.

The functioning of the PD-cycler described above occurs in accordance with known state of the art, in particular as described in WO 95/20985. The patient connects himself to the coupling 21f in a known way and the PD-cycler is activated for emptying the patient of used PD-fluid. This occurs by the scales container 6 being subjected to an under-pressure and the valve pack opens the valve 64d which acts on the tube 24b for emptying the spent PD-fluid to the drain bag in the PD-cycler during an drain phase. The drain bag is continually weighed, whereby the machine can determine when the patient is drained. The machine is programmed to drain a predetermined amount corresponding to the filled amount plus the expected ultrafiltration. Additionally it is an indication that the patient is empty when the drain flow starts to decrease.

Prior to this the PD-cycler has filled fresh PD-fluid to the heater bag in a predetermined amount by subjecting the scales container to an under-pressure at the same time as the valve pack opens the valve 64b which acts on the tube 22a (or the valve 64a which acts on the tube 19a). The fresh PD-fluid is heated up in the heater bag to about 37° C. After the drain phase the contents of the heater bag is filled to the patient in a filling phase by the valve pack opening the valve 64c which acts on the tube 24a and in that an over-pressure is arranged in the scales container. Finally the contents of the drain bag is transferred to the collection bag 16 by the valve pack opening the valve 64e which acts on the tube 19f while the over-pressure is present in the scales container. It should be understood that the sequence of operations can be varied within certain limits, as described in WO 95/20985.

When the treatment has been finalised and the patient is disconnected from the PD-cycler, it happens that the supply bags 15a-15e have not been emptied completely. Additionally, certain remains can also be left over in the heater and drain bags. In accordance with the present invention, an emptying of the supply bags and the heater bag is performed in the following way. While the under-pressure is being created in the scales container, valves 64a and 64b are opened (the other valves are closed) to thereby completely empty any remaining contents in the supply bags 15a-15e to the heater bag. Then, an over-pressure is created in the scales container and the separate valve 64f is opened at the same time as the valve 64e is open and other valves are closed. In that way, the contents of the heater bag is pumped directly to the collection bag 16 and the tube set's supply bags and the heater bag are entirely emptied of fluid.

Alternatively, the valve 64f can be open at the same time as the valves 64a and 64b are open and the contents in the supply bags 15a-15e is emptied both to the heater bag and the drain bag. Then both of these bags are emptied to the collection bag or any waste receiver.

The valve 64f does not have to be arranged in connection with the other valves but instead can be located anywhere between the valve pack and the heater bag and the drain bag. The important thing is that the valve opens a direct connection between the heater bag and the drain bag, or alternatively a direct connection between the heater bag and the collection bag 16. An alternative position is at the through-guide 23. This valve can even be manually actuated or can be achieved through the use of tube clamps.

FIG. 1 shows the use of a separate collection bag 16. Often however, supply bags which have been used in a previous tube set and which have been emptied, are used as the collection bag. It is therefore of great importance that the supply bags are truly emptied so that when they are used as collection bags, they have full capacity.

In order to allow use of spent supply bags as the collection bag 16, the tube 22a is provided with a luer-coupling 22b, by means of which the supply bags can be separated from the previous tube set. When using as collection bag the luer-coupling 22b is connected to the coupling 21g.

FIG. 9 shows a scales container 6 which is positioned inside the PD-cycler. The scales container is supported on one or more load cells 10 so that its weight can be read off. The scales container is positioned in a pressure vessel 7 inside the PD-cycler, which is pressure-tight sealed by means of the cover 11 and a seal 9. An air pump 19 is connected to the pressure container 7 and can achieve an under-pressure or an over-pressure therein of suitable size, such as +/−100 mm Hg. The seal 9 has a recess 8 which co-operates with the through guide 23 in the tube set.

The scales container 6 consists of a substantially rectangular container 72 with an upwardly facing opening 73 on one side. When the cover 11 in the PD-cycler's casing is pivoted upwardly, this opening 73 is exposed so that a combined heater and drain bag 27, 28 can be introduced into the container 72. The bottom of the scales container includes a heater foil 20 or other heater element, so that the contents in the heater bag can be heated up to a suitable temperature, about 37° C.

The combined heater and drain bag 27, 28 must have a sufficiently large volume for containing both the fresh PD-fluid which is to be fed into the patient in the heater bag and the used PD-fluid which is fed out of the patient to the drain bag. Therefore the bags are dimensioned to contain in total a maximum of about 8-10 liters. Such a bag is relatively large and bulky and is difficult to handle.

Figure 11:
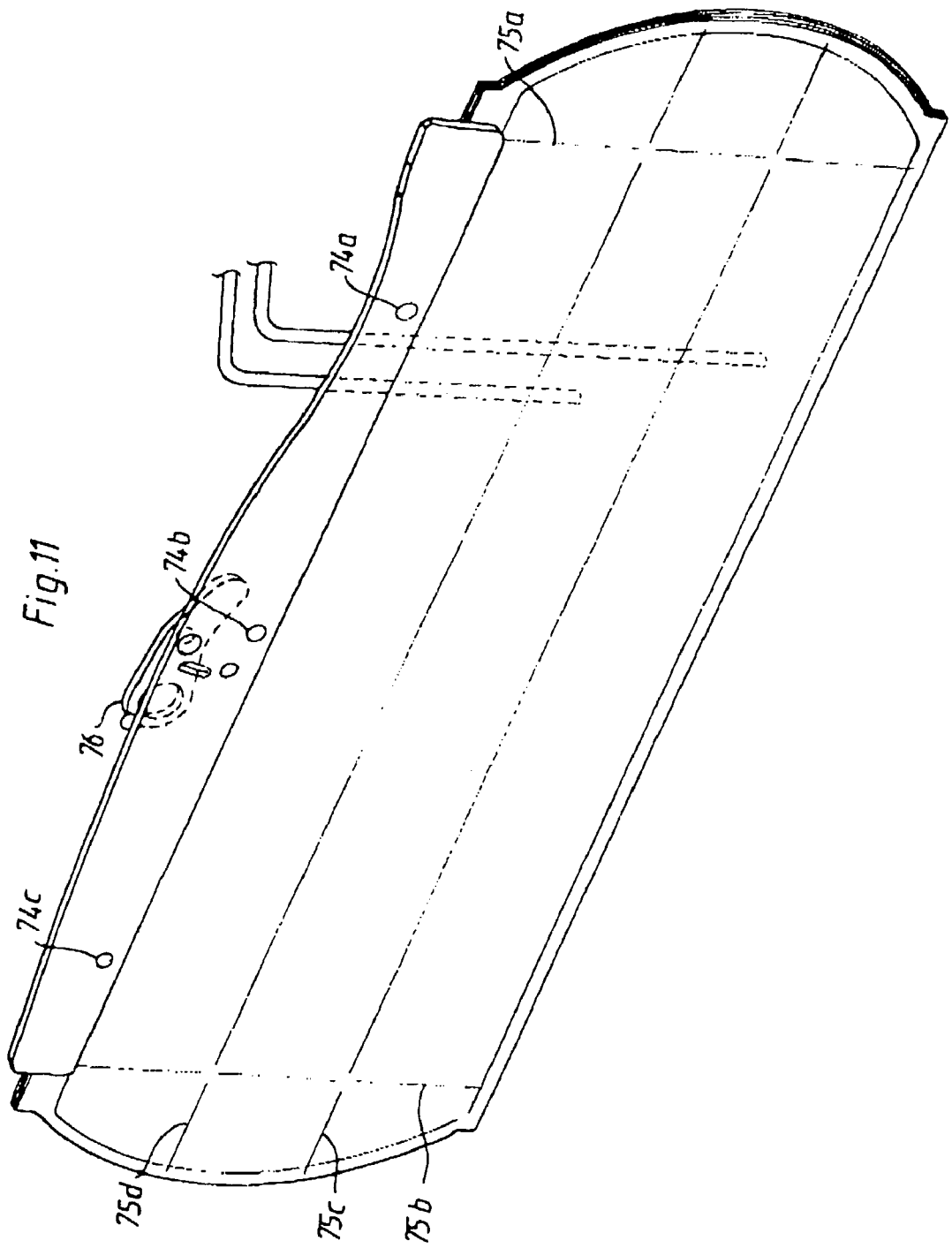
FIG. 11 is a perspective view of the heater bag and the drain bag in the tube set according to FIG. 2.

In accordance with the present invention the handling of the bag is made easier by the bag being arranged on a yoke 29 as is shown in FIG. 2 and in more detail in FIGS. 10 and 11. The bags are fixed to the yoke by means of three rivets 74a, 74b, 74c. The bags are of semi-rigid plastics material and consist of three layers, for which reason the bags together will be relatively easy to handle.

Figure 14:
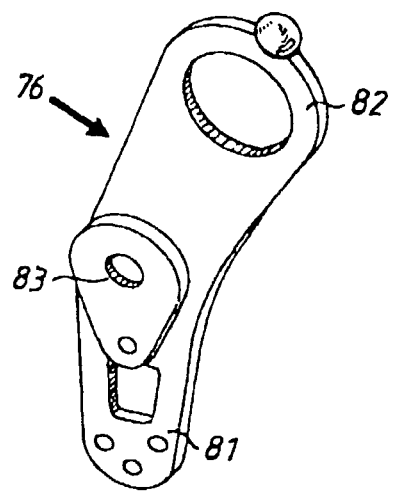
FIG. 14 is a perspective view of a hook bracket which is included in the tube set.

The bags are folded together along four fold lines 75a, 75b, 75c, 75d. Firstly the short sides of the bags are folded along the folding lines 75a and 75b. Then the bags are folded upwardly along the fold line 75c and then additionally one time upwards along line 75*d*. The fold line 75*c* will then end up at the upper edge of the bag and a holder member 76 is arranged to maintain the bag in the folded up position during normal handling and storage. The holder member 76 is shown in more detail in FIG. 14 and consists of a lower part 81 which maintains the bag, and an upper part 82 which is somewhat angled relative to the lower part. When the bags are positioned inside the scales container, the patient manoeuvres the holder member in order to release the bag so that it can fold up by itself inside the scales container. Alternatively, or if the patient has forgotten to release the bag, when the cover 11 is closed, the cover can co-operate with the upper part 82 and press it downwards, whereby the whole holder member 76 rotates around an axis 83. In this way the co-operation between the lower part 81 of the holder member 76 is released and the bag is free to fold up on itself inside the scales container.

In the folded-up state, it is easy to introduce the bags into the opening 73 in the scales container when the cover 11 is open. The introduction is simplified also by the scales container being provided with two guides 77 and 78 at the short edges of the opening, one of said guides being shown in more detail in FIG. 12. The guide 78 is provided with a somewhat slanted guide surface 79 which becomes successively more slanted and finally opens into a shaft 80. The shaft 80 is dimensioned to be able to house and maintain the short end of the yoke 29 so that the yoke 29 is vertically orientated as shown in FIG. 10.

The entire tube set, which is shown in FIG. 2, is positioned in a sterile enclosure and is sterilised, normally with ethylene dioxide. When the tube set is taken out of the sterile enclosure, the organizer 3 is of essential importance for easily putting in the tube set in the PD-cycler without tangling the tubes together. Then, the tubes can be connected one after the other to respective bags whilst other couplings are held in position by the organizer. In this way a tube set is obtained which is easy to handle, this often being of major importance for a PD-patient, who can be old and have difficulties in moving his hands and fingers.

In an alternative embodiment of the tube set, the combined heater and drain bag is made with a volume which is adapted to the normally occurring volume which is about 2-3 liters per bag, i.e. the double bag has a volume of 4-6 liters. In this way, the scales container and the whole PD-cycler can be manufactured correspondingly smaller, whereby about 4 liters or more in volume can be stored in the PD-cycler.

For those patients who use larger replacement volumes than 2-3 liters, such as 3.5 liters, a sequential emptying is used instead by the patient. Assume that the double bag has a volume of 5 liters. First the heater bag is filled with the intended fill volume, in this case 3.5 liters. Then the patient is drained, but the drain bag can only hold 1.5 liters. When 1.5 liters is drained of the patient, the drain stops and the PD-machine is adjusted to emptying the contents in the drain bag to the waste receiver, such as the collection bag 16. Thereafter, a second drain of the patient of an additional 1.5 liters occurs, which is then emptied to the collection bag. Finally, a last drain of the patient of 0.5 liters plus the ultrafiltrate of for example 0.3 liters occurs. After that, the fresh heated PD-fluid is fed into the patient.

This sequential draining of course takes a longer time than if the drain occurred in a single step, but can be motivated in order to reduce the size of the PD-cycler. Moreover, the heat energy in the drain fluid may be transferred to the fresh PD-fluid present in the fill bag, aiding in the heating of the fresh PD-fluid.

Figure 15:
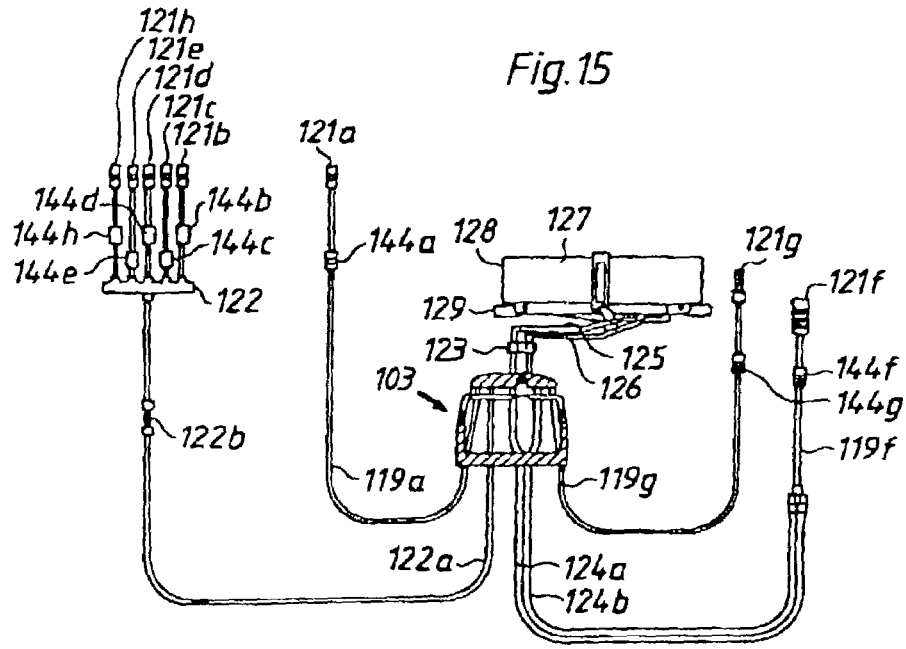
FIG. 15 is a schematical view of a variant of a tube set intended to be used on the PD-cycler of the invention.

In FIG. 15, there is shown a variant of the PD set intended to be used in the PD-cycler according to the invention. The same items as shown in FIG. 2 has obtained the same reference numeral added by 100. Thus, the tube set comprises a heater bag 127 and a drain bag 128 combined into a double bag, which is folded in the same way as described in connection with FIG. 11. The double bag is attached to a yoke 129. Two tubes 125 and 126 conduct fluid to and from the bags. The tubes 125 and 126 passes a through-guide 123 and to a combined connection unit and organizer 103. Tube 125 is divided into three tubes, tube 119*a* connected to a separate supply bag via connector 121*a*, tube 122*a* connected to several supply bags via a manifold 122 and several tube connectors 121*b*, 121*c*, 121*d*, 121*e*, 121*h*, and patient tube 124*b* connected to the patient via tube 119*f* and connector 121*f*. Tube 126 is divided into two tubes, namely patient tube 124*b* connected to the patient and emptying tube 119*g* connected to a collection bag or waste receiver via connector 121*g*.

All tubes ending in a connector are provided with clamps 144*a*, 144*b*, 144*c*, 144*d*, 144*e*, 144*f*, 144*g*, 144*h* to isolate the tube set from the surroundings before and after use.

Figure 16:
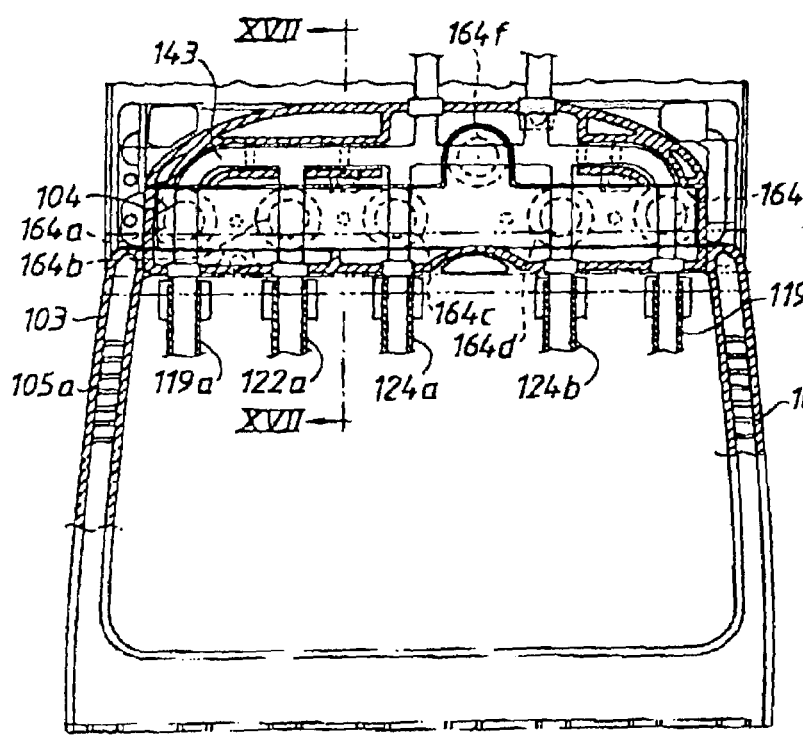
FIG. 16 is a cross-sectional view according to line XVI-XVI of FIG. 17 and shows an organizer of the tube set of FIG. 15 in an operating position on the PD-cycler.
Figure 17:
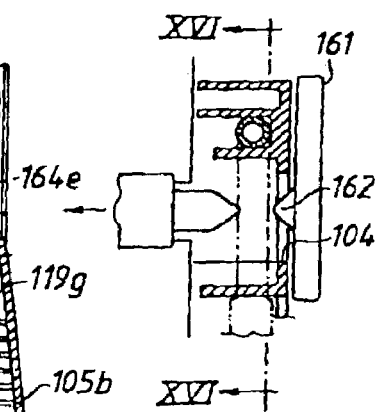
FIG. 17 is a cross-sectional view according to line XVII-XVII of FIG. 16.

The combined combined connection unit and organizer 103 is shown in more detail in FIGS. 16 and 17. FIG. 16 is taken according to line XVI-XVI in FIG. 17 and FIG. 16 is taken according to line XVII-XVII in FIG. 16. Thus, the top surface of the organizer is not visible in FIG. 16. As appears from FIG. 16, a dedicated tube connector set 143 is arranged instead of the different connectors 42 and 48 according to the embodiment of FIG. 4. The five tubes 119*a*, 122*a*, 124*a*, 124*b* and 119*g* are connected to the connector set 143. The organizer 103 comprises a central opening 104 through which the stems of the valve shafts 164*a*, 164*b*, 164*c*, 164*d*, 164*e* and 164*f* may extend. The cover 161 includes a longitudinal ridge 162 which is placed opposite of the valve shafts and extend into said opening 104, when the cover 161 is closed. Another transversal ridge (not visible in the drawings) extend transversally opposite the off-set valve shaft 164*f*. When the valve shafts are actuated, the influence upon tube sections of the dedicated connector set 143 and press these tube sections against the ridges of the cover. Thus, the corresponding tube sections are sealed off as required for the operation. The dedicated connector set 143 may be manufactured by a material different from the tubes, such as an elastomer, to better perform its function. The tubes are frequently made by PVC, which is very inexpensive.

The organizer portion in the bottom portion of FIG. 16 may be of similar construction as the embodiment shown in FIG. 3, but provided with a large central opening to reduce material. Moreover, the organizer bottom portion comprises weakening portions 105*a* and 105*b* so that the organizer may adapt its shape to the exterior of the PD-cycler during operation but may be arranged planar during storage.

Another version of the scales container is shown in FIGS. 18, 19 and 20. The container 106 is of the same general shape as the container 6 in the embodiment of FIGS. 9 and 10. In FIG. 18, there is shown a electric circuit board 107 attached to the exterior of the container for connection to the rest of the PD-cycler. FIG. 19 shows the container from the top and through the opening 109, the heater foil 110 is visible as well as two temperature sensors 111 and 112.

Moreover, in FIG. 19 is shown two light transmitters 120 and 121 arranged adjacent the opening 109, and two light receivers arranged opposite each a transmitter, as shown in FIGS. 19 and 20. The transmitters and receivers normally transmits and recieves light, since the path between each transmitter and each receiver should be free. If however, the heater and drain bags inside the container 106 become over-full, so that it extends above the level of the opening 109, one or both of the light path become obstructed and one or both of the light receivers indicates a fault condition. The transmitters and receivers may operate in the infrared wavelength area, because these devices are relatively inexpensive and operates well.

Figure 12:
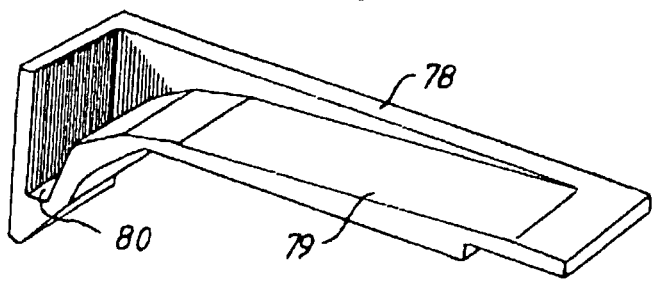
FIG. 12 is a perspective view of a guide arranged in the scales container according to FIG. 9.
Figure 13:
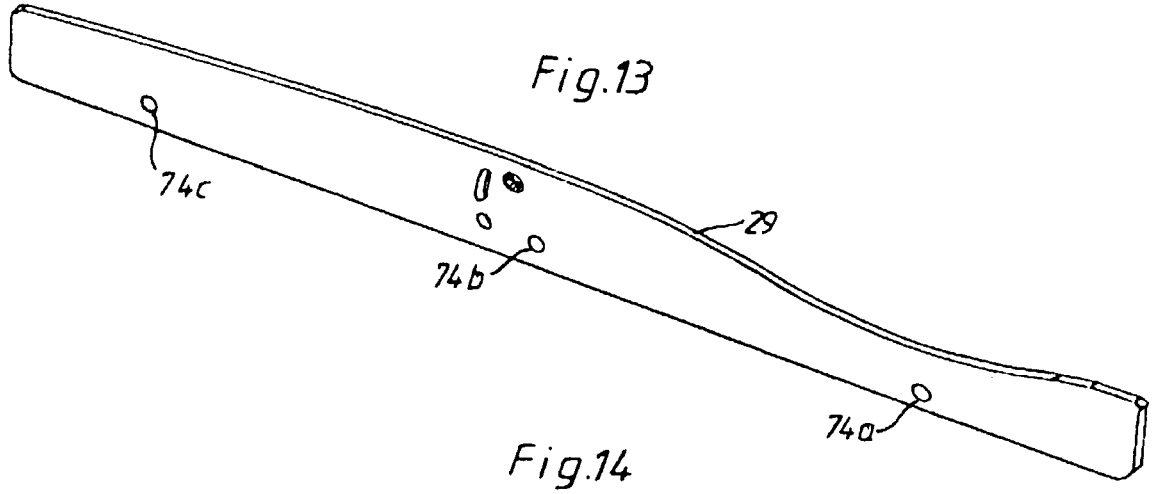
FIG. 13 is a perspective view of a yoke which a heater bag and a drain bag in the tube set of FIG. 2.

In FIG. 19 is moreover disclosed a variant of the guides 77 and 78 shown in the embodiment of FIGS. 9, 10 and 12. The variant guide 177 is shown in more details in FIGS. 21 and 22. Guide 177 comprises a recess 179 intended to enclose the end portion of the yoke of the tube set in use. The recess 179 comprises two shoulders 180 and 181 which limits the entrance area of the recess 179. When the yoke end portion has passed down into the recess, it is difficult to remove it because the shoulders 180, 181 resist such removal. As appears from FIG. 19, the container 106 is provided with a shoulder 182 in the middle of the opening 109. The shoulder 182 presses the yoke middle portion slightly outwards so that the yoke end portions engage below the shoulders 181 rather than below the shoulders 180. In this way, a safe and reliable operating position is obtained for the yoke.

The invention has been described above with reference to a preferred embodiment thereof and with reference to the embodiments of the invention shown in the drawings. The invention is however not limited to the shown details but the various components can be combined in different ways within the framework of the invention. The invention is limited only by the following claims.

The invention claimed is:

1. An apparatus for peritoneal dialysis (PD), comprising:
   a PD-cycler;
   a tube set connected to the PD-cycler;
   a PD-fluid source connected to the tube set;
   a heater bag connected, via the tube set, to the PD-fluid source, wherein the heater bag temporarily stores and heats the PD-fluid received from the PD-fluid source before introduction to a patient;
   a drain bag connected to the tube set, wherein the drain bag receives spent PD-fluid from the patient;
   a waste receiver connected to the tube set, wherein the waste receiver at least receives PD-fluid from the drain bag;
   a valve pack connected to the PD-cycler comprising a plurality of valves operable on the tube set to control flows of fluids through the tube set; and
   a transfer member arranged to connect the heater bag and the waste receiver,
   wherein one of the valves operable on the tube set operates to keep the transfer member closed during PD-treatment and open after completion of PD-treatment,
   wherein when the transfer member is open after completion of PD-treatment,
      the transfer member is configured to transfer the PD-fluid in the heater bag to the waste receiver, and
      the PD-fluid remaining in the PD-fluid source is directed via the transfer member to the waste receiver by actuation of at least another one of the valves operable on the tube set.

2. The apparatus of claim 1, wherein the PD-fluid source is at least one supply bag.

3. The apparatus of claim 1, wherein the waste receiver is a collection bag.

4. The apparatus of claim 1, wherein, after completion of the PD-treatment, the PD-fluid remaining in the PD-fluid source is first directed to the heater bag by actuation of at least one of the valves, and, after transfer of PD-fluid to the heater bag, actuation of at least one valve permits transfer of the PD-fluid from the heater bag to the waste receiver.

5. The apparatus of claim 1, further comprising:
   a scales container containing the heater bag and the drain bag, wherein the scales container permits an over-pressure or an under-pressure to be applied to the heater bag and the drain bag to assist with flow of the PD-fluid;
   a transfer member connecting the heater bag to the drain bag, wherein one valve in the valve pack operates on the transfer member to keep the transfer member closed except when PD-fluid from the heater bag is transferred to the waste receiver.

6. The apparatus of claim 1, wherein the valve pack comprises:
   a connection unit housing a portion of the tube set, the connection unit comprising a plurality of abutments each adjacent to one of the tubes in the tube set;
   a valve rod for each of the plurality of valves cooperating with the abutments, wherein each valve rod clamps a tube between itself and a corresponding abutment to control flow within the tube.

7. The valve apparatus of claim 6, wherein the valve rods are actuated in a gradual fashion to stop flow in the tubes, thereby achieving a soft valve operation.

8. The apparatus of claim 6, further comprising:
   a ferromagnetic rod, arranged to conduct magnetic radiation from a source of magnetism to a detector of magnetism, to indicate that the connection unit is positioned correctly.

9. The apparatus of claim 1, wherein the heater bag and the drain bag together form a double bag with three plastic layers welded together at edges thereof.

10. The apparatus of claim 9, further comprising:
    a yoke supporting the double bag along one side, wherein the double bag is folded along a fold line and is supported by a holding member on the yoke.

11. The apparatus of claim 1, further comprising:
    a pressure container enclosing the heater bag and the drain bag; and
    an indicator to indicate when the drain bag or the heater bag extends above an opening in the pressure container.

12. The apparatus of claim 11, wherein the indicator comprises:
    a light transmitter transmitting a light signal; and
    a light receiver disposed opposite to the light transmitter to detect an interruption in the light signal.

13. The apparatus of claim 12, wherein the light signal comprises an infrared component.

14. The apparatus of claim 12, wherein the light signal consists essentially of an infrared component.

15. An apparatus for peritoneal dialysis (PD), comprising:
    a PD cycler;
    a tube set connected to the PD cycler;
    a PD-fluid source connected to the tube set;
    a heater bag connected to the tube set for temporarily storing and heating PD-fluid received from the PD-fluid source;
    a drain bag connected to the tube set for receiving spent PD-fluid from a patient;
    a waste receiver connected to the tube set for receiving PD-fluid from the drain bag;
    a valve pack connected to the PD-cycler comprising a plurality of valves operable on the tube set to control flow of PD-fluid through the tube set; and
    a transfer member arranged to connect the heater bag and the waste receiver, wherein one of the plurality of valves operable on the tube set operates on the transfer member to keep the transfer member closed during PD-treatment and open after completion of PD-treatment, wherein when the transfer member is open after completion of PD-treatment, the transfer member is configured to transfer the PD-fluid in the heater bag to the waste receiver, and the PD-fluid from the PD-fluid source is permitted to flow via the heater bag to the waste receiver by actuation of at least another one of the valves operable on the tube set.

16. The apparatus of claim 15, wherein the tube set further comprises:

a first connection piece connected to the heater bag; and a second connection piece connected to the waste receiver, wherein the transfer member connects the first connection piece to the second connection piece.

17. The apparatus of claim 16, wherein the second connection piece connects to the drain bag, permitting PD-fluid to flow from the heater bag and the drain bag to the waste receiver.

18. The apparatus of claim 15, wherein the heater bag and the drain bag together form a double bag comprising three plastic layers welded together at edges thereof.

19. The apparatus of claim 18, further comprising:

a yoke comprising a holding member to support the double bag along one side, wherein the double bag is folded along a fold line and is supported by the holding member.

* * * * *